United States Patent [19]

Okumura et al.

[11] Patent Number: 4,481,373

[45] Date of Patent: Nov. 6, 1984

[54] METHOD OF MANUFACTURING KETONES

[75] Inventors: Yoshiharu Okumura, Tokyo; Tadamori Sakakibara; Katsumi Kaneko, both of Saitama, all of Japan

[73] Assignee: Toa Nenryo Kogyo Kabushiki Kaisha, Tokyo, Japan

[21] Appl. No.: 422,684

[22] Filed: Sep. 24, 1982

Related U.S. Application Data

[63] Continuation-in-part of Ser. No. 389,028, Jun. 16, 1982, abandoned.

[30] Foreign Application Priority Data

Jun. 28, 1982 [EP] European Pat. Off. ........ 82303361.8
Jul. 1, 1982 [JP] Japan ............................... 57-101333

[51] Int. Cl.$^3$ ............................................. C07C 45/35
[52] U.S. Cl. .................................... 568/401; 568/475; 568/910
[58] Field of Search ...................... 568/398.8, 408, 401, 568/360

[56] References Cited

U.S. PATENT DOCUMENTS 3,365,498  1/1968  Bryant et al. ........................ 568/360
3,365,499  1/1968  Clement et al. ..................... 568/408
3,370,073  2/1968  Clement et al. ..................... 260/406
3,475,461  10/1969  Lloyd .................................. 568/401
3,932,521  1/1976  Gloyer et al. ....................... 260/533

FOREIGN PATENT DOCUMENTS 1259145  1/1972  United Kingdom .

OTHER PUBLICATIONS

Ab. of Japanese Patent Publication No. 2010/1971.
Ab. of Japanese Patent Publication No. 21975/1972.
Ab. of Japanese Patent Publication No. 21402/1968.
Angew. Chem. 71, 176, (1959).
Hydrocarbon Process and Petroleum Refiner, 42, (7), 149, (1963).
Hydrocarbon Processing, Mar. 1976, p. 97.
Journal of Organic Chemistry, 29, 241, (1964).
Journal of Organic Chemistry, 34, 3949, (1969).
Journal of Organic Chemistry, 39, 3276, (1974).

*Primary Examiner*—James H. Reamer
*Attorney, Agent, or Firm*—Rebecca Yablonsky

[57] ABSTRACT

The invention relates to a method for the manufacture of ketones which comprises oxidizing an n-olefin in the presence of a catalyst containing palladium, copper, a halogen, and at least one of specific tertiary amines.

1 Claim, No Drawings

METHOD OF MANUFACTURING KETONES

CROSS-REFERENCE TO RELATED APPLICATION

This application is a continuation-in-part of U.S. Ser. No. 389,028, filed June 16, 1982, now abandoned.

BACKGROUND OF THE INVENTION

This invention relates to a method for the manufacture of ketones by the oxidation of an olefin, and more particularly to a method for efficient manufacture of a ketone by the oxidation of an n-olefin of at least four carbon atoms.

The so-called Hoechst-Wacker process which produces a carbonyl compound by the oxidation of an olefin in the presence of a palladium compound, a copper compound, a halogen and water has been known for a long time. By this process, acetaldehyde is produced from ethylene and acetone from propylene respectively on a commercial scale—see Angew. Chem. 71, 176 (1959); Hydrocarbon Process and Petroleum Refiner, 42 (7) 149 (1963) and Hydrocarbon Processing, March 1976, page 97.

For the manufacture of a ketone from a higher olefin of at least four carbon atoms, no process has yet been brought to practical application because (1) the reaction velocity is low, particularly for the internal olefin as compared with the terminal olefin, (2) the reaction entails occurrence of such secondary products as aldehyde and chlorinated ketone, and (3) the corrosion of the reaction apparatus by hydrogen chloride is violent.

A number of attempts have been made to date with a view to eliminating some of the problems which are involved in the process for the manufacture of a ketone from a higher olefin.

For example, a method for producing methylethyl ketone with improved yield and selectivity by effecting the oxidation of n-butene, preferably 2-butene, in the presence of an aqueous solution of palladium compound and ferric sulfate (Japanese Patent Publication Nos. 2010/1971 and 21975/1972 and Japanese Patent Publication No. 15811/1972 equivalent to GB No. 1,259,145), a method for producing methyl ketone in improved yield by effecting the oxidation of a higher terminal olefin in the presence of a solvent comprising an oxygen-containing compound such as alcohol, polyol, sulfolan, or dimethyl formamide [Journal of Organic Chemistry, 29, 241 (1964); ibid., 34, 3949 (1969); and ibid., 39, 3276 (1974)], and a method which effects the oxidation at a low temperature in the presence of a surface active agent to improve the selectivity of the conversion to the ketone aimed at (Japanese Patent Application Disclosure No. 16419/1979 equivalent to U.S. Pat. No. 4,152,354; see also U.S. Pat. No. 4,203,927) have been known to the art.

Even by these known methods, however, the aforementioned problems have not yet been thoroughly eliminated.

A method for increasing the rate of the carbonylation reaction by the incorporation of an amine or a hydrogen halogenide salt thereof into a catalyst formed of a palladium compound and copper salt (Japanese Patent Publication No. 21402/1968) is also known to the art.

Although this method resorts to use of a tertiary amine such as trimethylamine, triethylamine, or other trialkylamine, or triethanolamine, the effect obtainable by the use of such a tertiary amine is not significant.

U.S. Pat. No. 3,370,073 discloses the oxidation of olefins, preferably alpha-olefins, in the presence of palladium chloride, copper chloride, water and a solvent of certain solubilizing properties and certain dielectric strength such as methanol, dimethylformamide and dimethylacetamide but only when the olefins have at least six carbon atoms per molecule; see also U.S. Pat. Nos. 3,365,499 and 3,932,521.

SUMMARY OF THE INVENTION

The inventors have made a diligent study for the purpose of providing a commercially useful method for the manufacture of a ketone by the oxidation of an olefin, particularly a higher olefin. They have discovered that the velocity and the selectivity of the reaction can be improved and the corrosion of the reaction apparatus can be diminished by incorporation of a specific tertiary amine into the catalyst system containing palladium, copper, and a halogen.

This invention resides in a method for the manufacture of a ketone by effecting the oxidation of an n-olefin in the presence of a catalyst containing palladium, copper, a halogen and at least one of the tertiary amines represented by the general formulas,

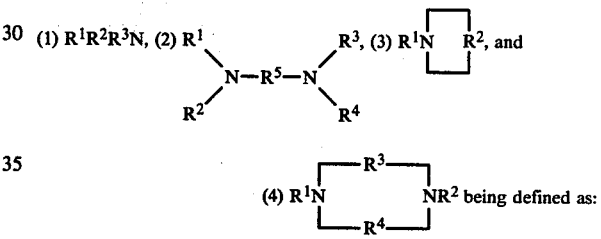

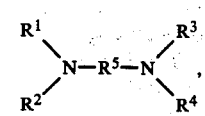

(1) general formula $R^1R^2R^3N$, wherein, $R^1$=an aryl of 6 to 20 carbon atoms, an aralkyl of 7 to 20 carbon atoms, or a substituted alkyl derived from an alkyl of 1 to 16 carbon atoms by the substitution of one or more hydrogen atoms of said alkyl with a halogen atom, an alkoxy of 1 to 12 carbon atoms, or an acyl of 2 to 16 carbon atoms, and $R^2$, $R^3$=an alkyl of 1 to 16 carbon atoms, an aryl of 6 to 20 carbon atoms, an acyl of 2 to 16 carbon atoms, an aralkyl of 7 to 20 carbon atoms, or a substituted alkyl derived from said alkyl by the substitution of one or more hydrogen atoms of said alkyl with a halogen atom, an alkoxy of 1 to 12 carbon atoms, or an acyl of 2 to 16 carbon atoms, provided that $R^2$ and $R^3$ may be identical, or not identical, with each other, (2) general formula, $$R^1\diagdown\phantom{N}\diagup R^3$$
$$N-R^5-N$$
$$R^2\diagup\phantom{N}\diagdown R^4$$

wherein, $R^1$, $R^2$, $R^3$, $R^4$=an alkyl of 1 to 16 carbon atoms, an aryl of 6 to 20 carbon atoms, an acyl of 2 to 16 carbon atoms, an aralkyl of 7 to 20 carbon atoms, or a substituted alkyl derived from said alkyl by the substitution of one or more hydrogen atoms of said alkyl with a halogen atom, an alkoxy of 1 to 12 carbon atoms, or an acyl of 2 to 16 carbon atoms, provided that $R^1$, $R^2$, $R^3$, and $R^4$ may be identical, or not identical, with one another, and $R^5=$ an alkylene of 1 to 8 carbon atoms, an arylene of 6 to 12 carbon atoms, or a group

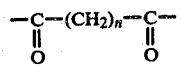

where n=2 to 4,
(3) general formula

wherein, $R^1=$ an alkyl of 1 to 16 carbon atoms, an aryl of 6 to 20 carbon atoms, an acyl of 2 to 16 carbon atoms, an aralkyl of 7 to 20 carbon atoms, or substituted alkyl derived from said alkyl by the substitution of one or more hydrogen atoms of said alkyl by a halogen atom, an alkoxy of 1 to 12 carbon atoms, or an acyl of 2 to 16 carbon atoms, and $R^2=$
 (A) an alkylene of 3 to 6 carbon atoms,
 (B) a substituted alkylene derived from said alkylene by the substitution with one or more of alkyl groups of 1 to 8 carbon atoms, aryl groups of 6 to 20 carbon atoms, aralkyl groups of 7 to 20 carbon atoms, or halogen atoms, and including a substituted alkylene having halogen atom substitution in substituent alkyl, aryl and aralkyl groups,
 (C) a formula, $-(CH_2)_m-O-(CH_2)_n-$ where m, n=1 to 5 and (m+n)=3 to 6, or
 (D) a formula,

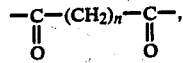

where n=2 to 4, and
(4) general formula,

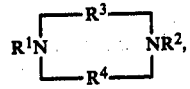

wherein, $R^1$, $R^2=$ an alkyl of 1 to 16 carbon atoms, an aryl of 6 to 20 carbon atoms, an acyl of 2 to 16 carbon atoms, an aralkyl of 7 to 20 carbon atoms, a substituted alkyl derived from said alkyl by the substitution of one or more hydrogen atoms of said alkyl by a halogen atom, an alkoxy of 1 to 12 carbon atoms, or an acyl of 2 to 16 carbon atoms, provided that $R^1$ and $R^2$ may be identical, or not identical with each other, and $R^3$, $R^4=$
 (A) an alkylene of 1 to 6 carbon atoms,
 (B) a substituted alkylene derived from said alkylene by the substitution of one or more hydrogen atoms of said alkylene by an alkyl of 1 to 8 carbon atoms, an aryl of 6 to 20 carbon atoms, an acyl of 2 to 16 carbon atoms, an aralkyl of 7 to 20 carbon atoms, or a halogen atom,
 (C) a formula, $-(CH_2)_m-O-(CH_2)_n-$, where m, n=1 to 5 and (m+n)=3 to 6,
 (D) a formula,

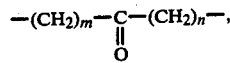

where m, n=0 to 5 and (m+n)=2 to 6, or
(E) a formula,

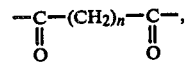

where n=2 to 4,
provided that $R^3$ and $R^4$ may be identical, or not identical, with each other.

Alternatively, the tertiary amines may be represented by the general formulas,

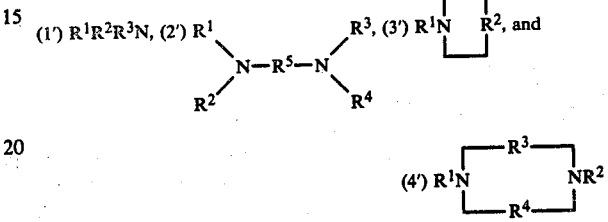

being defined as:
 (1') general formula $R^1R^2R^3N$, wherein, $R^1=$ an aryl of 6 to 20 carbon atoms, an aralkyl of 7 to 20 carbon atoms, or a substituted alkyl derived from an alkyl of 1 to 16 carbon atoms by the substitution of a hydrogen atom of said alkyl with a halogen atom, an alkoxy of 1 to 12 carbon atoms, or an acyl of 2 to 16 carbon atoms, and $R^2$, $R^3=$ an alkyl of 1 to 16 carbon atoms, an aryl of 6 to 20 carbon atoms, an acyl of 2 to 16 carbon atoms, an aralkyl of 7 to 20 carbon atoms, or a substituted alkyl derived from said alkyl by the substitution of a hydrogen atom of said alkyl with a halogen atom, an alkoxy of 1 to 12 carbon atoms, or an acyl of 2 to 16 carbon atoms, provided that $R^2$ and $R^3$ may be identical, or not identical, with each other,
 (2') general formula,

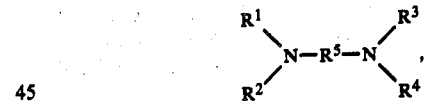

wherein, $R^1$, $R^2$, $R^3$, $R^4=$ an alkyl of 1 to 16 carbon atoms, an aryl of 6 to 20 carbon atoms, an acyl of 2 to 16 carbon atoms, an aralkyl of 7 to 20 carbon atoms, or a substituted alkyl derived from said alkyl by the substitution of a hydrogen atom of said alkyl with a halogen atom, an alkoxy of 1 to 12 carbon atoms, or an acyl of 2 to 16 carbon atoms, provided that $R^1$, $R^2$, $R^3$, and $R^4$ may be identical, or not identical, with one another, and $R^5=$ an alkylene of 1 to 8 carbon atoms or an arylene of 6 to 12 carbon atoms,
 (3') general formula

wherein, $R^1=$ an alkyl of 1 to 16 carbon atoms, an aryl of 6 to 20 carbon atoms, an acyl of 2 to 16 carbon atoms, an aralkyl of 7 to 20 carbon atoms, or a substituted alkyl derived from said alkyl by the substitution of a hydrogen atom of said alkyl by a halogen atom, an alkoxy of 1 to 12 carbon atoms, or an acyl of 2 to 16 carbon atoms, and $R^2 =$
(A) an alkylene of 3 to 6 carbon atoms,
(B) a substituted alkylene derived from said alkylene by the substitution of a hydrogen atom of said alkylene by an alkyl of 1 to 8 carbon atoms, an aryl of 6 to 20 carbon atoms, an aralkyl of 7 to 20 carbon atoms, or a halogen atom,
(C) a formula, $-(CH_2)_m-O-(CH_2)_n-$, where m, n=1 to 5 and (m+n)=3 to 6, or
(D) a formula,

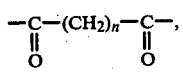

where n=2 to 4, and
(4') general formula,

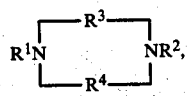

wherein, $R^1$, $R^2$=an alkyl of 1 to 16 carbon atoms, an acyl of 2 to 16 carbon atoms, an aralkyl of 7 to 20 carbon atoms, a substituted alkyl derived from said alkyl by the substitution of a hydrogen atom of said alkyl by a halogen atom, an alkoxy of 1 to 12 carbon atoms, or an acyl of 2 to 16 carbon atoms, provided that $R^1$ and $R^2$ may be identical, or not identical with each other, and $R^3$, $R^4 =$
(A) an alkylene of 1 to 6 carbon atoms,
(B) a substituted alkylene derived from said alkylene by the substitution of a hydrogen atom of said alkylene by an alkyl of 1 to 8 carbon atoms, an aryl of 6 to 20 carbon atoms, an acyl of 2 to 16 carbon atoms, an aralkyl of 7 to 20 carbon atoms, or a haloen atom,
(C) a formula, $-(CH_2)_m-O-(CH_2)_n-$, where m, n=1 to 5 and (m+n)=3 to 6,
(D) a formula,

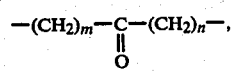

where m, n=0 to 5 and (m+n)=2 to 6, or
(E) a formula,

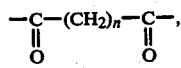

where n=2 to 4,
provided that $R^3$ and $R^4$ may be identical, or not identical, with each other.

DETAILED DESCRIPTION

Olefin

The olefins which are usable in the present invention are linear monoolefins of 3 to 12 carbon atoms, inclusive of terminal olefins having a carbon-carbon double bond in the terminal carbon-carbon bond of the olefin and internal olefins having the carbon-carbon double bond in an internal carbon-carbon bond of the olefin.

Specific examples of the olefins include propylene, 1-butene, 2-butene, 1-pentene, 2-pentene, 1-hexene, 2-hexene, 3-hexene, 1-heptene, 2-heptene, 1-octene, and 2-octene.

A feature of the invention is that those internal olefins which have never been used advantageously as raw materials for the conventional method because of their lower reaction velocity than terminal olefins can be utilized safely to produce corresponding ketones aimed at. In the conventional method, if an iso-olefin is contained in the raw material, the iso-olefin reacts preferentially and this reaction interferes with the oxidation of the n-olefin and, moreover, the reaction product of the iso-olefin is required to be removed from the main reaction product. In contrast, in accordance with the present invention, the n-olefin is selectively oxidized into a corresponding carbonyl compound. Thus, a further feature of the present invention is that a raw material containing an iso-olefin can be used safely.

The present invention, therefore, permits use of a raw material containing a terminal olefin, an internal olefin, and an iso-olefin in its unaltered form. Particularly, this invention proves advantageous for the manufacture of methylethyl ketone by using, as its raw material, the so-called $C_4$ fraction which contains iso-butene, 1-butene, and 2-butene.

If the raw material contains a paraffinic hydrocarbon, the hydrocarbon has absolutely no adverse effect. When the raw material contains a diolefinic or acetylenic unsaturated hydrocarbon, however, it is desirable that such hydrocarbon be removed or converted into a monoolefin through selective hydrogenation.

Catalyst

The catalyst to be used in the present invention contains palladium, copper, a halogen, and a specific tertiary amine.

(1) Palladium

Sources for palladium are palladium compounds. Of the palladium compounds, those preferably usable are palladium chloride, palladium bromide, palladium acetate, and palladium sulfate. Metallic palladium can be used when it is capable of forming any of the palladium compounds enumerated above in situ.

(2) Copper

Sources for copper are copper compounds. Of the copper compounds, those preferably usable are cupric chloride, cuprous chloride, cupric bromide, cuprous bromide, cupric sulfate, and cupric acetate. Metallic copper can be used when it is capable of forming any of the copper compounds enumerated above in situ.

(3) Halogen

As regards the halogen source, when the aforementioned palladium compound and/or copper compound is used in the form of a halogenide, the halogenide can be used as a halogen source. When neither palladium halogenide or copper halogenide is used or when such a halogenide is used in an amount not enough to fill a desired halogen supply, there can be used hydrogen halogenide such as hydrogen chloride or hydrogen bromide, a halogen such as chlorine or bromine, a halogenide of alkali metal such as sodium chloride, potassium chloride, lithium chloride, or potassium bromide, or a halogenide of alkaline earth metal such as calcium chloride, magnesium chloride, or calcium bromide.

(4) Tertiary Amine

The tertiary amine to be used in this invention is selected from the compounds represented by the above general formulas (1) through (4).

Examples of the compounds which are embraced by the general formula (1) given above are as follows.

Triphenylamine, diphenylmethylamine, phenyldimethylamine, tribenzylamine, dibenzylmethylamine, benzyldimethylamine, dibenzylphenylamine, diphenylbenzylamine, tri-(2-methoxyethyl)-amine, tri-(ethoxyethyl)-amine, tri-(2-chloroethyl)-amine, tri-(2-fluoroethyl)-amine, N,N-dimethyl-acetamide, N,N-diethyl-acetamide, N,N-dimethyl-benzamide, N-methylacetanilide, N,N-dimethyl-acetyl-acetamide.

Examples of the compounds which are embraced by the general formula (2) given above include, N,N,N',N'-tetraphenylethylene diamine, N,N,N',N'-tetramethyl-p-phenylene diamine, N,N,N',N'-tetrabenzylethylene diamine, N,N,N',N'-tetraacetyl-p-xylylene diamine, and N,N,N',N'-tetramethyl succinic acid amide.

Examples of the compounds which are embraced by the general formula (3) given above are as follows.

N-acetyl pyrrolidine, N-acetyl piperidine, N-phenyl pyrrolidine, N-phenyl piperidine, N-(2-chloroethyl)-pyrrolidine, N-(2-chloroethyl)-piperidine, N-acetylmethyl pyrrolidine, N-acetylmethyl piperidine, N-benzyl pyrrolidine, N-(methoxymethyl)-pyrrolidine, N-phenyl morpholine, N-acetyl morpholine, N-methyl morpholine, N-methyl-2-phenyl pyrrolidine, N-acetyl-2-phenyl pyrrolidine, N-methyl-2-trichloromethyl pyrrolidine, N-methyl-2-trichloromethyl piperidine, N-methylsuccinic acid imide, and N,2,2,6,6,-pentamethyl piperidine.

Examples of the compounds which are embraced by the general formula (4) given above are: N,N'-diacetyl piperazine, N,N'-diphenyl piperazine, N,N'-dimethyl-2,5-dioxo piperazine, N,N'-di-(2-chloroethyl)-2,5-diethyl piperazine, 1,7-dimethyl-1,7-diaza-4,10-dioxocyclododecane, and 1,5-dimethyl-1,5-diaza-2,4-dioxocycloheptane.

The catalyst to be used in the present invention contains palladium, copper, a halogen, and a specific tertiary amine. Generally, the catalyst is obtained by dissolving the compounds just mentioned in water.

The palladium content in this catalyst system is 0.1 to 100 milligram atom/liter, preferably 0.5 to 20 milligram atom/liter, as palladium. The copper content is 1 to 500 times, preferably 2 to 200 times, palladium in atomic ratio. The halogen content is 0.1 to 10 times, preferably 0.5 to 3 times, copper in atomic ratio. The specific amine content is such that the nitrogen content of the amine is 1 to 1,000 times, preferably 2 to 500 times, the halogen in atomic ratio.

Oxidation of Olefin

The method of this invention is accomplished by bringing the raw material containing an n-olefin into contact with the catalyst described above. As to the manner of this contact, either the one-step method which effects the contact in the presence of oxygen or the two-step method which comprises effecting the contact in the absence of oxygen and subsequently subjecting the catalyst to regeneration by oxidation, can be employed.

For the oxidation of the olefin, it is desirable that the olefin as the raw material and the catalyst are brought into thorough contact. Generally, such thorough contact is accomplished by a mechanical method which comprises mixing the two components and vigorously stirring the mixture.

For the purpose of facilitating the contacting of the two components, it may be effected in the presence of a solvent comprising an oxygen-containing organic compound.

Examples of solvents useful for this purpose include alcohols such as methanol and ethanol; polyols such as ethylene glycol and propylene glycol; ethers such as di-n-butyl ether and diisobutyl ether; polyalkylene glycols such as polyethylene glycol and polypropylene glycol; esters such as ethyl acetate and n-butyl acetate; ketones such as acetone and methylethyl ketone; and carboxylic acids such as formic acid and acetic acid.

The conditions for the oxidation of the olefin are 40° to 140° C., preferably 50° to 110° C. for reaction temperature; 1 to 50 atmospheres, preferably 3 to 20 atmospheres for reaction pressure; and 15 minutes to 10 hours, preferably 0.5 to 5 hours for reaction time. In the one-step process, the partial pressure of oxygen is suitably 1 to 15 atmospheres. The ratio of mixing between the olefin and the catalyst is 10 to 500 moles, preferably 20 to 300 moles, of the olefin in the two-step process, or 50 to 2,000 moles, preferably 100 to 1,000 moles, of the olefin in the one-step process, respectively per one gram atom of palladium contained in the catalyst.

The contacting of the olefin with the catalyst may be effected either batchwise or continuously and in a multiplicity of steps or in one step.

The ketone produced by the method of this invention can be isolated and recovered from the reaction system by any of the methods generally employed for treatments of this nature.

Effect of the Invention

The present invention possesses outstanding effects as described below.

(1) The oxidation of the linear olefin proceeds quickly. In particular, the rate of oxidation of a higher n-olefin having four or more carbon atoms is high as compared with the rate obtainable by the conventional method. Thus, this invention permits commercialization of the production of a ketone from a higher n-olefin.

(2) The production of an aldehyde due to the oxidation of the terminal carbon atom in an α-olefin is inhibited and the conversion to methyl ketone is promoted. Thus high selectivity to the ketone is obtained.

(3) The oxidation of the internal olefin proceeds quickly and the selectivity to the ketone is high. The invention, therefore, can select the raw material from a wide range of hydrocarbons.

(4) The oxidation of iso-olefin is inhibited. This means that the removal of iso-olefin from the hydrocarbon being used as the raw material, a step indispensable to the conventional method, can be omitted.

(5) The formation of such secondary products as chlorinated ketone is inhibited. This means that the step for removal of such secondary products can be simplified and the purity of the produced ketone can be improved.

(6) The corrosion of the reaction apparatus is diminished.

The invention will now be described in further detail with reference to the following examples which do not limit the scope of the invention.

EXAMPLE 1

An autoclave of stainless steel lined with polytetrafluoroethylene was charged with 1 millimole of palladium chloride, 100 millimoles of cupric chloride, 400 millimoles of diphenylmethylamine, and 1 liter of water. With 50 millimoles of propylene incorporated under pressure, the contents of the autoclave were vigorously stirred at 70° C. for one hour to effect oxidation of propylene. At the end of the reaction, the autoclave was suddenly cooled to expel the unconverted propylene.

When the reaction mixture was analyzed, the conversion of propylene was found to be 38%, the selectivity to acetone to be 99.4%, and the selectivity to chloroacetone to be 0.2%.

EXAMPLE 2

1-butene as the starting olefin was oxidized by following the procedure of Example 1, except that N,N,N',N'-tetraphenylethylenediamine was used as the tertiary amine. The results are shown in Table 1.

EXAMPLE 3

2-butene as the starting olefin was oxidized by following the procedure of Example 1, except that tri-($\beta$-chloroethyl)-amine was used as the tertiary amine. The results are shown in Table 1.

COMPARATIVE EXPERIMENTS 1–3

The procedures of Examples 1–3 were repeated to effect oxidation of the respective olefins, except that the respective tertiary amines were not used. The results are shown in Table 1.

EXAMPLE 4

The same autoclave that was used in Example 1 was charged with 2 millimoles of palladium chloride, 20 millimoles of cupric chloride, 50 millimoles of tribenzylamine, and 1 liter of water. With 0.5 mole of propylene incorporated under pressure and oxygen further incorporated under pressure to a partial pressure of 5 atmospheres, the contents of the autoclave were vigorously stirred to effect the reaction of propylene with oxygen. At the end of the reaction, the reaction mixture was analyzed. The results are shown in Table 2.

To determine the corroding property of the catalyst, the oxidation was carried out in the presence of a carbon steel piece 2.0 g in weight and 35 cm² in surface area. At the end of the oxidation, the carbon steel piece was weighed to find the loss due to corrosion. The results are also shown in Table 2.

EXAMPLES 5–8

The procedure of Example 4 was repeated, except that the olefin and the tertiary amine were varied as shown in Table 2. The results are shown in Table 2.

COMPARATIVE EXPERIMENTS 4–8

The procedures of Examples 4–8 were repeated, except that the respective tertiary amines were not used. The results are shown in Table 2.

COMPARATIVE EXPERIMENTS 9 AND 10

2-butene was oxidized by following the procedure of Example 6, except that the tertiary amine used in Example 6 was varied to the tertiary amines shown in Table 2. The results are shown in Table 2.

TABLE 1

| Example | Olefin | Tertiary amine | Conversion of olefin (%) | Ketone | Aldehyde | Chlorinated ketone |
|---|---|---|---|---|---|---|
| Example 1 | Propylene | Diphenylmethylamine | 38 | 99.4[1] | 0.4[3] | 0.2[5] |
| Example 2 | 1-Butene | N,N,N',N'—tetraphenylethylenediamine | 27 | 99.7[2] | 0.5[4] | 0.1[5] |
| Example 3 | 2-Butene | Tri-($\beta$-chloroethyl)-amine | 18 | 99.7[2] | 0.1[4] | 0.2[5] |
| Comparative Experiment 1 | Propylene | — | 25 | 90[1] | 8[3] | 2 |
| Comparative Experiment 2 | 1-Butene | — | 14 | 87[2] | 10[4] | 3[5] |
| Comparative Experiment 3 | 2-Butene | — | 9 | 92[2] | 5[4] | 3[5] |

(Note)
[1] Acetone
[2] Methylethyl ketone
[3] Propion aldehyde
[4] 1-Butanal
[5] Total of 1-chloro-2-butanone and 3-chloro-2-butanone

TABLE 2

| Example | Olefin | Tertiary amine Name | Amount used (millimoles) | Conversion (%) | Ketone | Aldehyde | Chlorinated ketone | Loss of test piece (g) |
|---|---|---|---|---|---|---|---|---|
| Example 4 | Propylene | Tribenzylamine | 50 | 39 | 90.6[1] | 1.2[7] | 0.2 | 0.01 |
| Example 5 | 1-Butene | N—phenyl piperidine | 60 | 16 | 99.0[2] | 0.9[8] | 0.1[11] | <0.01 |
| Example 6 | 2-Butene | N,N'—diphenyl piperazine | 80 | 13 | 99.9[2] | <0.1[8] | 0.1[11] | <0.01 |
| Example 7 | 1-Hexene | N,N,N',N'—tetraphenylethylene diamine | 50 | 7.0 | 90.7[3] | 1.1[9] | 0.2[12] | <0.01 |
| Example 8 | 1-Octene | N,N'—diphenyl piperazine | 50 | 5.8 | 99.0[4] | 0.9[10] | 0.1[13] | <0.01 |
| Comparative Experiment 4 | Propylene | — | — | 16 | 91[1] | 7[7] | 2 | 0.26 |
| Comparative Experiment 5 | 1-Butene | — | — | 8.1 | 89[2] | 8[8] | 3[11] | 0.28 |
| Comparative Experiment 6 | 2-Butene | — | — | 4.2 | 94[2] | 5[8] | 1[11] | 0.25 |
| Comparative | 1-Hexene | — | — | 3.4 | 87[5] | 9[9] | 4[12] | 0.29 |

TABLE 2-continued

| Example | Olefin | Tertiary amine Name | Amount used (millimoles) | Conversion (%) | Selectivity (%) Ketone | Aldehyde | Chlorinated ketone | Loss of test piece (g) |
|---|---|---|---|---|---|---|---|---|
| Experiment 7 Comparative | 1-Octene | — | — | 3.1 | 86[6] | 9[10] | 5[13] | 0.24 |
| Experiment 8 Comparative | 2-Butene | Triethylamine | 50 | 0.5 | — | — | — | <0.01 |
| Experiment 9 Comparative | 2-Butene | Tri-n-butylamine | 50 | 0.2 | — | — | — | <0.01 |
| Experiment 10 | | | | | | | | |

(Note)
[1] Acetone
[2] Methylethyl ketone
[3] 96.7% of 2-Hexanone and 2.0% of 3-hexanone
[4] 96.9% of 2-Octanone, 2.0% of 3-octanone, and 0.1% of 4-octanone
[5] 65% of 2-Hexanone and 22% of 3-hexanone
[6] 53% of 2-Octanone, 22% of 3-Octanone, and 11% of 4-octanone
[7] Propion aldehyde
[8] 1-Butanal
[9] 1-Hexanal
[10] 1-Octanal
[11] Total of 1-chloro-2-butanone and 3-chloro-2-butanone
[12] Total of 1-chloro-2-hexanone, 3-chloro-2-hexanone, 2-chloro-3-hexanone, and 4-chloro-3-hexanone
[13] Total of 1-chloro-2-octanone, 3-chloro-2-octanone, 2-chloro-3-octanone, 4-chloro-3-octanone, 3-chloro-4-octanone, and 5-chloro-4-octanone

EXAMPLES 9-11

By following the procedure of Example 4, 0.5 mole of 2-butene and a catalyst containing 2 millimoles of a varying palladium compound and 20 millimoles of a varying copper compound both shown in Table 3 and a varying amount of a tertiary amine and a varying amount of water both shown in Table 3 were brought into contact with each other under varying reaction conditions shown in Table 3 to effect oxidation of 2-butene. The results are shown in Table 3.

EXAMPLES 12-14

The procedure of Example 1 was repeated, except a varying tertiary amine was used in a varying amount both shown in Table 4 and 100 millimoles of a C$_4$ fraction consisting of 39 mole % of iso-butene, 30 mole % of 1-butene, 17 mole % of 2-butene, 8 mole % of iso-butane, and 6 mole % of n-butane was used.

The results of the oxidation are shown in Table 4.

COMPARATIVE EXPERIMENT 11

By following the procedure of Example 12, the same C$_4$ fraction was oxidized, except the tertiary amine was not used. The results are shown in Table 4.

TABLE 3

| Example | Palladium compound | Copper compound | Tertiary amine (amount used, mole) | Water (ml) | Other additive | Reaction temperature (°C.) | Partial pressure of oxygen (atm.) | Conversion (%) | Selectivity (%) Methylethyl ketone | n-Butyr aldehyde | Chloro- butanone | Loss of weight in test piece (g) |
|---|---|---|---|---|---|---|---|---|---|---|---|---|
| 9 | PdCl$_2$ | CuCl$_2$ | N,N,N',N'— tetramethyl succinic acid amide[8] | 200 | — | 100 | 5 | 83 | 99.1 | 0.8 | 0.1 | 0.01 |
| 10 | PdBr$_2$ | CuCl | N,N—dimethyl acetamide[8] | 150 | — | 70 | 5 | 71 | 99.9 | 0.1 | <0.1 | <0.01 |
| 11 | Pd(OAc)$_2$ (Note 1) | Cu(OAc)$_2$ (Note 2) | N,N'—diacetyl piperazine[8] | 300 | HCl (0.1 mole) | 65 | 2 | 57 | >99.9 | <0.1 | <0.1 | <0.01 |

(Note 1) Palladium acetate
(Note 2) Cupric acetate

TABLE 4

| | Tertiary amine | | Conversion (%) | | Selectivity based on n-butene (%) | | | Selectivity based on iso-butene (%) | |
|---|---|---|---|---|---|---|---|---|---|
| Example | Name | Amount used (mole) | n/Buten | Iso-butene | Methylethyl ketone | n-Butyr aldehyde | Chloro- butanone | Tertiary butyl alcohol | Iso-butyr aldehyde |
| Example 12 | Diphenylmethylamine | 0.4 | 21 | 1.1 | 99.3 | 0.5 | 0.2 | 50 | 50 |
| Example 13 | Tribenzylamine | 0.5 | 24 | 0.9 | 99.5 | 0.4 | 0.1 | 40 | 60 |
| Example 14 | N,2,2,6,6-pentamethyl piperidine | 0.6 | 23 | 1.0 | 99.4 | 0.5 | 0.1 | 50 | 50 |
| Comparative Experiment 11 | — | | 11 | 26 | 89 | 8 | 3 | 97 | 3 |

EXAMPLE 15-20

In the presence of 4 millimoles of palladium chloride, 40 millimoles of cupric chloride, 1 liter of water, and a varying amount of a varying tertiary amine both shown in Table 5, iso-butene and 1-butene or 2-butene used each in an amount of 0.5 mole were oxidized by following the procedure of Example 4. The results are shown in Table 5. In each of the examples, a carbon steel piece was used to test the catalyst for its corrosion property.

COMPARATIVE EXPERIMENTS 12-15

The same oxidation of butenes as involved in Examples 15-20 was carried out by following the procedure of such examples, except that either the tertiary amines involved therein were not used or varying tertiary amines shown in Table 5 were used. The results are shown in Table 5.

COMPARATIVE EXPERIMENT 16

The same $C_4$ fraction as used in Example 21 was oxidized by following the procedure of the example, except that N,N,N',N'-tetramethyl succinic acid amide was not used and the amounts of copper compound and water and the reaction temperature were varied as shown in Table 6 for one hour. The results are shown in Table 6.

TABLE 5

| | Butene mixture (mole) | | | | Conversion (%) | | Selectivity based on n-butene (%) | | | Selectivity based on iso-butene (%) | | Loss of weight in test piece (g) |
|---|---|---|---|---|---|---|---|---|---|---|---|---|
| Example | Iso-butene | 1-Butene | 2-Butene | Tertiary amine (millimole) | n-Butene | Iso-butene | Methyl-ethyl ketone | n-Butyl aldehyde | Chloro-butanone | Tertiary butyl alcohol | Iso-butyl aldehyde | |
| Example 15 | 0.5 | 0.5 | — | Diphenylmethylamine (100) | 16 | 1.2 | 99.0 | 0.9 | 0.1 | 60 | 40 | 0.01 |
| 16 | 0.5 | 0.5 | — | N,N,N',N'—tetramethyl-p-phenylene diamine (120) | 15 | 1.0 | 99.1 | 0.8 | 0.1 | 50 | 50 | <0.01 |
| 17 | 0.5 | 0.5 | — | N,2,2,6,6-pentamethyl piperidine (150) | 15 | 0.9 | 98.9 | 1.0 | 0.1 | 50 | 50 | <0.01 |
| 18 | 0.5 | — | 0.5 | Diphenylmethylamine (100) | 13 | 1.0 | 99.8 | 0.1 | 0.1 | 60 | 40 | 0.01 |
| 19 | 0.5 | — | 0.5 | N,N'—diphenyl piperazine (120) | 12 | 0.8 | 99.8 | 0.2 | <0.1 | 40 | 60 | <0.01 |
| 20 | 0.5 | — | 0.5 | N,2,2,6,6-pentamethyl piperidine (150) | 13 | 1.0 | 99.8 | 0.1 | 0.1 | 50 | 50 | <0.01 |
| Comparative Experiment 12 | 0.5 | 0.5 | — | — | 9.3 | 17 | 88 | 9 | 3 | 93 | 7 | 0.26 |
| 13 | 0.5 | — | 0.5 | — | 5.1 | 16 | 95 | 4 | 1 | 92 | 8 | 0.24 |
| 14 | 0.5 | 0.5 | — | Triethylamine (100) | <0.1 | <0.1 | — | — | — | — | — | <0.01 |
| 15 | 0.5 | — | 0.5 | Tri-n-butylamine (100) | <0.1 | <0.1 | — | — | — | — | — | <0.01 |

EXAMPLES 21-23

TABLE 6

| Example | | Palladium compound (millimole) | Copper compound (millimole) | Tertiary amine (mole) | Water (ml) | Reaction temperature (°C.) | Partial pressure of oxygen (atm) |
|---|---|---|---|---|---|---|---|
| Example | 21 | PdCl$_2$ (2) | CuCl$_2$ (40) | N,N,N',N'—tetramethyl succinic acid amide (8) | 200 | 100 | 5 |
| | 22 | PdBr$_2$ (2) | CuCl (40) | N,N—dimethyl acetamide (7) | 200 | 70 | 2 |
| | *23 | Pd(OAc)$_2$ | Cu(OAc)$_2$ (20) | N,N'—diacetyl piperazine (5) | 350 | 65 | 2 |
| Comparative Experiment | 16 | PdCl$_2$ (2) | CuCl$_2$ (20) | | 1,000 | 75 | 5 |

| Example | | Conversion (%) | | Selectivity based on n-butene (%) | | | Selectivity based on iso-butene (%) | | Loss of weight in test piece (g) |
|---|---|---|---|---|---|---|---|---|---|
| | | n-Butene | Iso-butene | Methyl-ethyl ketone | n-Butyl aldehyde | Chloro-butanone | Tertiary butyl alcohol | Iso-butyl aldehyde | |
| Example | 21 | 86 | 1.2 | 99.0 | 0.9 | 0.1 | 50 | 50 | 0.01 |
| | 22 | 74 | 0.8 | 99.7 | 0.3 | <0.1 | 60 | 40 | <0.01 |
| | *23 | 62 | 0.7 | 99.8 | 0.2 | <0.1 | 50 | 50 | <0.01 |
| Comparative Experiment | 16 | 3.2 | 15 | 90 | 8 | 2 | 91 | 9 | 0.22 |

*50 millimoles of HCl added. Pd(OAc)$_2$—Palladium acetate Cu(OAc)$_2$—Cupric acetate By following the procedure of Example 4, a catalyst containing 2 millimoles of a varying palladium compound shown in Table 6, and varying amounts of a varying copper compound shown in Table 6, a varying tertiary amine shown in Table 6, and water (with hydrogen chloride additionally used in Example 23) and 1 mole of a $C_4$ fraction consisting of 38 mole % of iso-butene, 32 mole % of 1-butene, 16 mole % of 2-butene, 8 mole % of iso-butane, and 6 mole % of n-butane were held in contact with each other under the conditions

EXAMPLE 24

By following the procedure of Example 4, a catalyst consisting of 6 millimoles of palladium chloride, 40 millimoles of cupric chloride, 120 millimoles of tri-β-chloroethylamine, and 1 liter of water and 1 mole of a pentene mixture consisting of 12% by weight of 1-pentene, 40% by weight of 2-pentene, 3% by weight of 3-methyl-1-butene, 37% by weight of 2-methyl-2-butene, and 8% by weight of 2-methyl-1-butene were held in contact with each other under the conditions of 3 kg/cm² of oxygen partial pressure and 80° C. of reaction temperature for five hours. The results are shown in Table 7.

COMPARATIVE EXPERIMENT 17

The same pentene mixture as used in Example 24 was oxidized by following the procedure of the example, except that tri-β-chloroethylamine was not used. The results are shown in Table 7.

TABLE 7

| Example | Conversion (%) | | Selectivity based on n-pentene (%) | | | | Selectivity to tertiary aryl alcohol based on iso-pentene (%) |
| --- | --- | --- | --- | --- | --- | --- | --- |
| | n-Pentene | Iso-pentene | 2-Pentanone | 3-Pentanone | n-Valer-aldehyde | Chloro-Pentanone | |
| Example 24 | 96.2 | 1.0 | 59.8 | 39.2 | 0.2 | 0.8 | 99 |
| Comparative Experiment 17 | 30.4 | 27.5 | 55.5 | 31.5 | 3.7 | 9.3 | 99 |

What is claimed is:

1. In a method for the manufacture of acetone or methyl ethyl ketone by oxidizing propylene or a n-butene optionally in admixture with isobutylene in the presence of water and a catalyst comprising a palladium compound, a copper compound and a halogen, at a temperature in the range of 40° to 140° C. and a pressure in the range of 1 to 50 atmospheres, the improvement which comprises incorporating in the reaction system at least one tertiary amine selected from the group consisting of diphenylmethylamine, tri-(β-chlorethyl) amine, tribenzylamine, N,N,N',N'-tetraphenylethylenediamine, N,N,N'N'-tetramethyl-p-phenylene diamine, N,N,N',N'-tetramethyl succinic acid amide, N-phenyl piperidine, N,2,2,6,6-pentamethyl piperidine, N,N'-diphenyl piperazine and N,N'-diacetyl piperazine.

* * * * *